United States Patent
Prasad

(10) Patent No.: US 11,642,389 B2
(45) Date of Patent: May 9, 2023

(54) **COMPOSITION AND METHOD OF *CAMELLIA SINENSIS* EXTRACT FOR WEIGHT MANAGEMENT**

(71) Applicant: Kodimule Shyam Prasad, Bangalore (IN)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 0 days.

(21) Appl. No.: 16/580,982

(22) Filed: Sep. 24, 2019

(65) Prior Publication Data

US 2020/0093881 A1 Mar. 26, 2020

Related U.S. Application Data

(60) Provisional application No. 62/736,399, filed on Sep. 25, 2018.

(51) Int. Cl.
| | | |
|---|---|---|
| *A61K 36/82* | (2006.01) | |
| *A23F 3/16* | (2006.01) | |
| *A23L 33/00* | (2016.01) | |
| *A61K 9/00* | (2006.01) | |
| *A61K 9/68* | (2006.01) | |
| *A61K 9/20* | (2006.01) | |
| *A61K 9/48* | (2006.01) | |

(52) U.S. Cl.
CPC ............. *A61K 36/82* (2013.01); *A23F 3/16* (2013.01); *A23L 33/30* (2016.08); *A61K 9/006* (2013.01); *A61K 9/0058* (2013.01); *A61K 9/0095* (2013.01); *A61K 9/20* (2013.01); *A61K 9/4808* (2013.01)

(58) Field of Classification Search
None
See application file for complete search history.

(56) References Cited

U.S. PATENT DOCUMENTS

2016/0140288 A1* 5/2016 Kuan ................. G16B 50/30
702/19
2018/0042287 A1* 2/2018 Mehansho .............. A23L 33/40

OTHER PUBLICATIONS

Buchholz, T. et al. Medicinal Plants Traditionally Used for Treatment of Obesity and Diabetes Mellitus. Phytotherapy Research 30(2)260-266, Dec. 2015. (Year: 2015).*
Lin, Y. et al. Determination of Tea Polyphenols and Caffeine in Tea Flowers (*Camellia sinensis*) and Their Hydroxyl Radical Scavenging and Nitric Oxide Suppressing Effects. J of Agricultural and Food Chemistry 57:975-980 2003. (Year: 2003).*
Yoshikawa M. et al. Acylated Oleanane Type Triterpene Saponins with Acceleration of Gastrointestinal Transit and Inhibitory Effect on Pancreatic Lipase from Flower Buds of Chinese Tea Plant. Chemistry & Biodiversity 6(6)903-915 Jun. 2009. (Year: 2009).*
Matsuda, H. New Biofunctional Effects of the Flower Buds of Camellia sinensis and its Bioactive Acylated Oleanane Type Triterpene Oligoglycosides. J Natual Medicines 70:689-701, Jul. 2016. (Year: 2016).*
Vieira-Ameida E. et al. Camellia sinensis Extract Inhibits In vitro Pancreatic Lipase and has Preventive Effect on Obesity in Female Rat Fed a High Fat Diet. African J of Pharmacy and Pharmacology 9(37)919-928, Oct. 2015. (Year: 2015).*
Furuyashiki T. et al. Tea Catechin Suppresses Adipocyte Differentiation . . . Bioscience, Biotechnology, and Biochemistry 68(11) 2353-2359, 2004. (Year: 2004).*

* cited by examiner

*Primary Examiner* — Ralph J Gitomer
(74) *Attorney, Agent, or Firm* — TMB Law; Timothy M. Brown

(57) ABSTRACT

The invention is directed to a composition comprising a green tea flower extract and methods for making and using the composition in the management of a healthy body weight. The composition can comprise an aqueous alcohol extract of *Camellia sinensis* that is administered to a patient to provide a method for maintaining a healthy body weight.

21 Claims, 5 Drawing Sheets

COMPOSITION AND METHOD OF *CAMELLIA SINENSIS* EXTRACT FOR WEIGHT MANAGEMENT

CROSS-REFERENCE TO RELATED APPLICATIONS

This application claims the benefit of U.S. Provisional Application No. 62/736,399, filed Sep. 25, 2018, the entire contents of which are incorporated herein by reference for all purposes.

FIELD OF THE INVENTION

The invention is in the field of preparations for weight management.

BACKGROUND

Green tea (*Camellia sinensis* L) prepared from tea leaves is one of the most widely consumed non-alcoholic beverages in the world. It has attained significant attention owing to its benefits against array of health problems such as obesity, diabetes mellitus, cardiovascular disorders, and cancer. These beneficial effects have been partly attributed to its chemical ingredients, including epigallocatechinin-3-gallate, epicatechinin-3-gallate, epigallocatechinin, and epicatechinin to name a few. The present disclosure and accompanying data enable a novel application of green tea, including the use of green tea flowers in the formulation of a composition for weight management.

SUMMARY OF THE INVENTION

It is an object of the invention to provide a composition formulated from green tea flower for the management of body weight.

In some aspects, the composition comprises green tea flower extract.

It is a further object of the invention to provide a method of modulating body weight comprising administering to a patient in need thereof a composition comprising green tea flower extract.

DEFINITIONS

Figure 1:
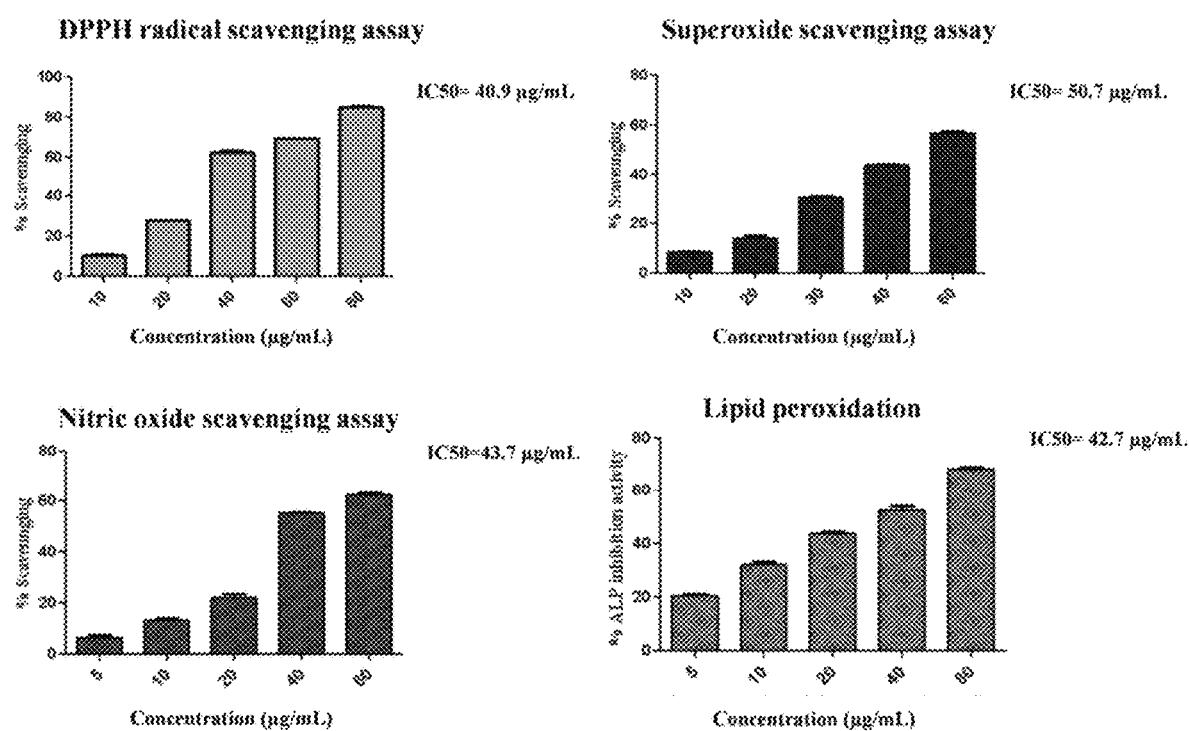
FIG. 1 depicts graphs showing the free radical scavenging activity of an embodiment the inventive composition.

As used herein, the term "about" means the quantity, level, value, number, frequency, percentage, dimension, size, amount, weight or length that is referenced, or that varies (plus or minus) by as much as 30%, 25%, 20%, 15%, 10%, 9%, 8%, 7%, 6%, 5%, 4%, 3%, 2% or 1% of the referenced quantity, level, value, number, frequency, percentage, dimension, size, amount, weight or length.

Throughout this specification, unless the context requires otherwise, the words "comprise," "comprises," and "comprising" will be understood to refer to the inclusion of a stated step or element, or group of steps or elements, but not the exclusion of any other step or element or group of steps or elements.

As used herein, the term "increase" refers to any measurable increase in a parameter relative to control conditions.

As used herein, the term "modulate" refers to the act of effecting an alteration or change in the natural state of a parameter or condition. For example, "modulate" can refer to an increase, decrease, the inhibition of, or preventing a change in, the body weight or body fat of a patient.

As used herein, the term "reduce" refers to any measurable decrease in a parameter relative to control conditions.

As used herein, the terms "subject," "patient," "individual" and like terms are used interchangeably and refer to, except where indicated, mammals such as humans and non-human primates, as well as livestock and companion and laboratory research animals.

DETAILED DESCRIPTION

The invention generally relates to the management of body weight. More particularly, the invention relates to a composition formulated from green tea flower extract and a method of its use and manufacture in the management of body weight.

The inventor surprisingly discovered a composition of green flower tea extract can be highly effective in managing a patient's body weight. As exemplified by the present disclosure, the composition has demonstrated effects on many aspects of the physiological regulation of body weight. In particular, the inventor has shown that the composition can inhibit pancreatic lipase and alpha amylase and impact adipocyte development. The inventor further demonstrated that the composition can impact the expression and activity of proteins involved in weight metabolism, including the transcription factors PPARγ and C/EBPα which are known adipogenesis regulators.

In some aspects, the invention provides a composition. The composition can comprise green tea flower extract. The composition can comprise green tea extract and one or more excipient or one or more carriers. In some aspects, the composition is free of an extract of green tea leaves. The composition can comprise green tea extract and one or more excipient and one or more carriers. The excipient and/or carrier can be selected on the basis of compatibility with green tea flower extract and the properties of the desired dosage form. Suitable excipients include, but are not limited to, binders, fillers, bulking agents, flow aids/glidents, disintegrants, lubricants, stabilizers, surfactants, and the like. The excipient can be selected from the group consisting of binders, fillers, bulking agents, flow aids/glidents, disintegrants, lubricants, stabilizers, surfactants, and combinations thereof. Suitable excipients and carriers for use with the composition include, but are not limited to, those disclosed in: Remington: The Science and Practice of Pharmacy, 19$^{th}$ Ed (Easton, Pa.: Mack Publishing Company, 1995); Hoover, John E., Remington's Pharmaceutical Sciences, (Easton, Pa.: Mack Publishing Co 1975); Liberman, H. A. and Lachman, L., Eds., Pharmaceutical Dosage Forms (New York, N.Y.: Marcel Decker 1980); and Pharmaceutical Dosage Forms and Drug Delivery Systems, Seventh Ed (Lippincott Williams & Wilkins 1999). The entire contents of these publications are incorporated herein by reference for all purposes.

In some aspects of the invention, the composition employs controlled, sustained, or extended release formulations known collectively as "modified release" formulations. The composition can be administered by modified release systems or by delivery devices known to those skilled in the art. Suitable examples of such systems and delivery devices include, but are not limited to, those described in the following patents, the entire disclosures of which are incorporated herein by reference for all purposes: U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; and 5,733,566. Dosage forms for the composition can be used to provide modified release of one or more active ingredients using, for example, hydropropylmethyl cellulose, other polymer matrices, gels, permeable membranes, osmotic systems, multilayer coatings, microparticles, liposomes, microspheres, or combinations thereof.

At least one aspect of the invention concerns the dosage form of the composition. The composition can be in the form of a powder, liquid, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol, injection, or combinations thereof. The composition can be formulated for oral administration. The composition can be combined with vitamins, minerals, amino acids, proteins, extracts, carbohydrates, lipids, fatty acids, caffeine, flavorings, sweeteners, preservatives, or combinations thereof.

In some aspects of the invention, the composition is combined with a food, snack, nutritional supplement, dietary supplement, food supplement, or beverage. The food, snack, nutritional supplement, dietary supplement, food supplement, or beverage can have reduced calorie content. For example, the composition can be provided as a means for managing body weight wherein the composition is formulated to provide a dietetic food, a dietetic snack, a dietetic nutritional supplement, a dietetic dietary supplement, a dietetic food supplement, or a dietetic beverage. The composition can be combined with dietetic snacks such as bars, chips, chews, gels, candies, chocolates, cakes, cookies and other pastries, wafers, crackers, ice cream, and the like.

The composition can be provided in bulk quantities for the industrial manufacture of the products and dosage forms described herein. For example, the composition can be provided in bulk quantities as a powder or liquid. Bulk quantities of the composition can be packaged, stored and/or distributed in drums, bags, boxes, and other containers which are configured to prevent or inhibit the oxidation of one or more active components of the composition.

In some aspects, the invention provides a method of modulating body weight in a patient. The method can be practiced by administering to the patient the composition of the present invention. In some preferred embodiments, the composition is administered in an effective amount. The composition can be administered to the patient to reduce body weight, or to inhibit or prevent weight gain in the patient. For example, the composition can be administered to maintain a desired body weight in the patient. Administering the composition can reduce body fat in the patient, or inhibit or prevent an increase in body fat in the patient. The patient can be obese, overweight or have a normal body weight. The terms "obese" and "obesity" as used herein refer to a patient having a body mass index of 30 or higher. The term "overweight" as used herein refers to a patient having a body mass index of 25 to 29.9. The term "healthy weight" as used herein refers to a patient having a body mass index of 18.5 to 24.9. In at least one aspect of the invention, the patient is human.

Without being limited to any particular theory or mechanism, administering the composition can impart its effect by, among other means, inhibiting one or more forms of lipase in the patient. Lipases (e.g. triacylglycerol hydrolase E.C. 3.1.1.3) are enzymes that catalyze the hydrolysis of ester bonds of triacylglycerols (fats and oils) to produce free fatty acids such as diacylglycerols, monoglycerols and glycerol. In the small intestine of mammals, the digestion of dietary triacylglycerols (TAG) is essentially due to the action of pancreatic lipase. The end products of TAG digestion are absorbed by the body and are responsible for the development of weight gain and obesity. Therefore, if the hydrolysis of TAG and its movement from the intestinal lumen into the body is stopped or minimized, the prevalence of obesity can be reduced. The composition can inhibit pancreatic lipase, pancreatic lipase related protein 2, hepatic lipase, endothelial lipase, lipoprotein lipase, or combinations thereof. In one non-limiting embodiment, administering the composition inhibits pancreatic lipase in the patient.

At least one aspect of the invention concerns the dosage at which the composition is administered to the patient. The composition can be administered at a dose of between about 5 mg/day and about 500 mg/day. The composition can be administered at a dose between about 20 mg/day and about 1 mg/day. The composition can be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition can be administered at a dosage of between about 400 mg/day and about 500 mg/day, between about 300 mg/day and about 400 mg/day, between about 200 mg/day and about 300 mg/day, between about 100 mg/day and about 200 mg/day, or about 20 mg/day and about 100 mg/day. It is contemplated that the composition can be administered at any dosage that intervenes the dosages called out in this specification.

In some aspects, the dosage of the composition is determined by the body weight of the patient. The composition can be administered between about 5 mg/kg b.w. and about 500 mg/kg b.w. The composition can be administered at about 5 mg/kg b.w., about 10 mg/kg b.w., about 20 mg/kg b.w., about 30 mg/kg b.w., about 40 mg/kg b.w., about 50 mg/kg b.w., about 60 mg/kg b.w., about 70 mg/kg b.w., about 80 mg/kg b.w., about 100 mg/kg b.w., about 120 mg/kg b.w., about 140 mg/kg b.w., about 160 mg/kg b.w., about 180 mg/kg b.w., about 200 mg/kg b.w., about 220 mg/kg b.w., about 240 mg/kg b.w., about 260 mg/kg b.w., about 280 mg/kg b.w., about 300 mg/kg b.w., about 320 mg/kg b.w., about 340 mg/kg b.w., about 360 mg/kg b.w., about 380 mg/kg b.w., about 400 mg/kg b.w., about 420 mg/kg b.w., about 440 mg/kg b.w., about 460 mg/kg b.w., about 480 mg/kg b.w., or about 500 mg/kg b.w. In one non-limiting embodiment of the invention, the composition is administered at about 150 mg/kg b.w. The composition can be administered, one, two, three, four, five or more times. The composition can be administered daily, weekly, monthly, or combinations thereof. The composition can be administered one, two, three, four, five, six or more times per day, per week, or per month. One skilled in the art will appreciate that the administration of the composition can be adjusted according to the patient's response to the treatment and the body weight desired by the patient or attending physician.

At least one aspect of the invention concerns the administration route of the composition. The composition can be administered systemically. Suitable administration routes for the composition include, but are not limited to, auricular, buccal, conjunctival, cutaneous, dental, endocervical, endosinusal, endotracheal, enteral, epidural, extra-amniotic, interstitial, intra-abdominal, intra-amniotic, intra-arterial, intra-articular, intrabiliary, intrabronchial, intrabursal, intracardiac, intracartilaginous, intracaudal, intracavernous, intracavitary, intracerebral, intraci sternal, intracorneal, intracoronal dental, intracoronary, intracorporus cavernosum, intradermal, intradiscal, intraductal, intraduodenal, intradural, intraepidermal, intraesophageal, intragastric, intravaginal, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravitreal, laryngeal, nasal, nasogastric, ophthalmic, oral, oropharyngeal, parentera, percutaneous, periarticular, peridural, perineural, periodontal, rectal, inhalation, retrobulbar, soft tissue, subarachnoid, subconjunctival, subcutaneous, sublingual, submucosal, topical, transdermal, transmucosal, transplacental, transtracheal, transtympanic, ureteral, urethral, vaginal, or combinations thereof. In a preferred embodiment, the composition is administered orally.

In at least one aspect, the invention provides a method for making the composition. The composition can be made by providing green tea flowers, and extracting one or more constituents effective in modulating body weight in the subject. The green tea flowers for making the composition can be flowers from *Camellia sinensis*. The green tea flowers can be fresh, dried, or a combination thereof. The extract can be made using any suitable process, including, without limitation, solvent extraction, extrusion, or a combination thereof. Suitable solvents for obtaining extracts for formulating the composition include, but are not limited to, aqueous solvents, alcohol-based solvents, supercritical fluids, polar organic solvents (such as acetone and methylethyl ketone), or combinations thereof. Non-limiting examples of alcohol-based solvents include, but are not limited to, ethanol, isopropyl alcohol, methanol, and combinations thereof. The supercritical fluid can be, but is not necessarily limited to, carbon dioxide.

The present disclosure is further described in the light of the following example which is set forth for illustration purposes only and is not to be construed as limiting the scope of the present invention.

EXAMPLE

Sample Preparation

A hydro alcoholic extract of green tea flower of *Camellia sinensis* was prepared and dissolved in water at the appropriate concentrations.

DPPH Free Radical Scavenging Activity

DPPH Free radical scavenging activity of green tea flower extract (GTFE) was carried out by adopting the protocol described by Braca et al., 2001.

Superoxide Anion Scavenging Activity

Superoxide anion scavenging activity of GTFE was carried out by the procedure described by McCord and Fridovich, 1969.

Nitric Oxide Scavenging Activity

Nitric oxide generated from sodium nitroprusside was measured by the Griess reagent by adopting the method described by Marcocci et al. 1994.

Anti-Lipid Peroxidation Assay (TBARS)

A modified thiobarbituric acid reactive species (TBARS) assay was used to measure the lipid peroxide formed using egg yolk homogenates as lipid-rich media, as described by Ruberto et al., 2000.

Pancreatic Lipase Activity

Pancreatic lipase activity of GTFE was measured by adopting the method described by Kim Y S et al., 2010 with minor modifications. Briefly an enzyme buffer was prepared by the addition of a solution of porcine pancreatic lipase (2.5 mg/ml in 10 mM MOPS (morpholinepropanesulphonic acid) and 1 mM EDTA, pH 6.8) to 169 µl of Tris buffer (100 mM Tris-HCl and 5 mM CaCl2, pH 7.0). Subsequently, 20 µl of different concentrations of GTFE was mixed with 20 µl of the enzyme buffer and incubated for 15 min at 37° C. with 5 µl of the substrate solution (10 mM p-NPB (p-nitrophenyl butyrate) in dimethyl formamide). The enzymatic reactions were allowed to stand for 30 min at 37° C. Lipase activity was determined by measuring the hydrolysis of p-NPB to p-nitrophenol at 405 nm using microplate reader.

α-Amylase Inhibition Assay

This assay was carried out using a modified procedure (McCue and Shetty, 2004). A total of 2500_, of extract (µg/mL) was placed in a tube and 250 µL of 0.02 M sodium phosphate buffer (pH 6.9) containing α-amylase solution (0.5 mg/mL) was added. This solution was pre-incubated at 25° C. for 10 min, after which 250 µL of 1% starch solution in 0.02 M sodium phosphate buffer (pH 6.9) was added at timed intervals and then further incubated at 25° C. for 10 min. The reaction was terminated by adding 500 µL of dinitrosalicylic acid (DNS) reagent. The tubes were then incubated in boiling water for 3 min and cooled to room temperature. The reaction mixture was diluted with 5 mL distilled water and the absorbance was measured at 540 nm using spectrophotometer. A control was prepared using the same procedure replacing the GTFE with distilled water. The α-amylase inhibitory activity was calculated as a percentage inhibition.

Cell Culture and Differentiation

3T3-L1 fibroblasts were cultured to confluence in Dulbecco's modified Eagle medium (DMEM) supplemented with 10% (v/v) fetal bovine serum (FBS:BCO) and 1% penicillin-streptomycin (GIBCO) in a $CO_2$ incubator at 37° C. On day 2 post-confluence (designated as day 0), cells were induced to differentiate with DMEM containing 10% fetal bovine serum (FBS; GIBCO), 5 µg/ml insulin (Sigma, St. Louis, Mo., USA), 1 µmol/L dexamethasone (Sigma), and 0.05 mmol/L 3-isobutyl-1-methylxanthine (IBMX; Sigma) (MDI cocktail). After 2 days, the medium was replaced with DMEM supplemented with 10% FBS and 5 µg/ml insulin. The cells were subsequently re-fed every 48 h with DMEM containing 10% FBS. To examine the anti-adipogenic effect of GTFE, GTFE was added to the medium at different concentrations (10, 25, 50, and 100 µg/ml) during medium changes.

MTT Assay

3T3-L1 fibroblasts were seeded at a density of 1×10$^4$ cells/well in 96-well plates. The cells were treated with different concentrations of GTFE for 48 h. After completion of the treatment, the cells were incubated with 0.5 mg/ml MTT (3-4,5-dimethylthiazol-2-yl-2, 3-diphenyl tetrazolium bromide) for 4 h at 37° C. The supernatants were carefully aspirated and 100 µL of DMSO was added to dissolve the formazan crystal product. Absorbance was measured at 560 nm using a microplate reader.

Oil Red O Staining

Adipocyte cell monolayers were gently rinsed twice with phosphate-buffered saline (PBS), fixed in a with 4% paraformaldehyde-PBS solution for 1 h at room temperature, stained with 0.5% Oil Red O isopropyl alcohol for 1 h, and then washed with distilled water. The cells were checked by a bright-field optical microscope (HS-100, OPTICAL, China). The cells were eluted with isopropyl alcohol and absorbance was measured at 520 nm with a microplate reader.

Western Blot Analysis

Cells were harvested by scraping in 120 µL lysis buffer (RIPA). They were then incubated on ice for 20 min and centrifuged at 13,000 rpm for 15 min. The supernatant was then transferred to a fresh tube. Protein concentrations were determined. Equal concentrations of protein (100 m per lane) were loaded in the wells of 6-12% polyacrylamide gels. After the electrophoretic run, proteins on gels were transferred to a polyvinylidene difluoride membrane (Millipore, Marlborough, Mass., USA) and incubated in 5% non-fat milk at room temperature. The membrane was incubated with PPARγ (Abcam, 1:500), C/EBPα (Cell Signaling Technology, 1:1000), and β-actin (Santa Cruz Biotechnology, 1:200) overnight at 4° C. The blots were incubated with horseradish peroxidase-conjugated secondary antibody (Santa Cruz Biotechnology) for 1 h. The blots were developed by enhanced chemiluminescence (Santa Cruz Biotechnology).

Statistical Analysis

Each experiment was repeated three times and the data averaged for reporting. Data is given as the mean±standard error. Statistical analysis of data was determined by analysis of variance (ANOVA). All statistical tests were performed at the P<0.05 of significance.

Results

Reactive oxygen species (ROS), such as hydroxyl radicals, superoxide anions, and hydrogen peroxide can cause oxidative damage to cellular biomolecules. High levels of reactive oxygen species are intricately linked to obesity and associated pathologies, notably insulin resistance and type 2 diabetes. In this study, free radical scavenging activity of the composition of the invention was carried out using different in vitro models. The results of DPPH, superoxide anion, nitric oxide scavenging properties of GTFE are shown in FIG. 1.

DPPH Radical Scavenging Activity

GTFE showed concentration dependent DPPH radical scavenging activity (FIG. 1) with an IC50 value 40.9 µg/mL. The effect of antioxidants on DPPH radical scavenging was thought to be due to their hydrogen donating ability.

Superoxide Anion Scavenging Activity

The results of this study showed a concentration-dependent pattern for the scavenging of superoxide anion radicals. GTFE distinctly showed scavenging ability and an IC 50 value found to be 50.7 µs/mL (FIG. 1)

Nitric Oxide Scavenging Activity

GTFE inhibited the formation of nitric oxide from sodium nitroprside. A dose dependent pattern for nitric oxide scavenging potential was exhibited by GTFE (FIG. 1). For scavenging nitric oxide radicals, GTFE showed an IC50 of 43.7 µg/mL Inhibition of Lipid Peroxidation GTFE was analyzed for its ability to inhibit lipid peroxidation. The generation of malondialdehyde (MDA) and related substances that react with thiobarbituric acid was found to be inhibited by GTFE (FIG. 1). The IC50 value of GTFE for lipid peroxidation was found to be 42.7 µg/mL.

Effect on Pancreatic Lipase and Amylase Activity

Figure 2:
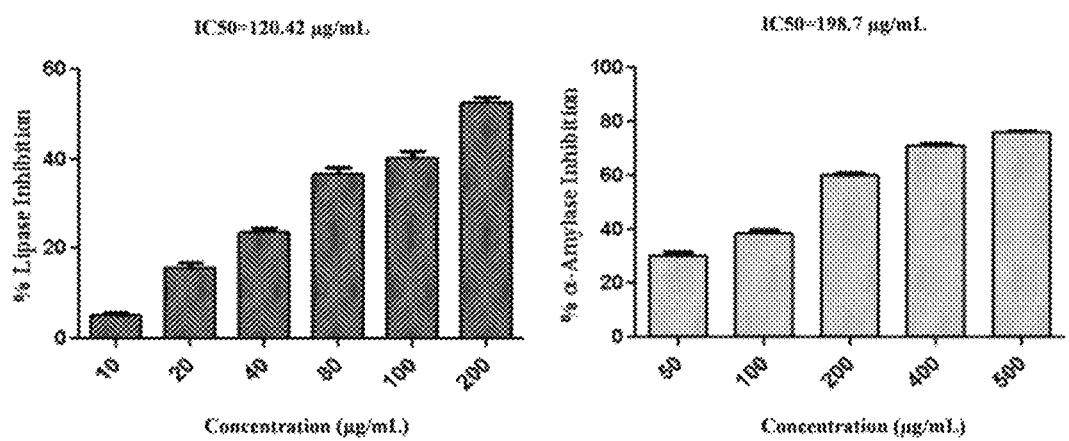
FIG. 2 depicts graphs showing the inhibitory effect of an embodiment of the inventive composition on pancreatic lipase and alpha amylase.

FIG. 2 presents GTFE's effect on pancreatic lipase and α-amylase activity. GTFE showed a concentration dependent inhibitory activity towards pancreatic lipase and α-amylase, the calculated IC50 value for pancreatic lipase and α-amylase activity were 120.42 and 198.7 µg/mL respectively. The lipase activity in digestive system breaks down dietary fats and oils into free fatty acids. These free fatty acids are absorbed into the blood stream and occur in circulation as triglycerides. The increased level of serum triglycerides provides a marker for altered lipid metabolism in the body. In the present study, GTFE showed inhibitory activity. Inhibition of the enzyme alpha-amylase decreases the hydrolysis of starch into simple sugars. Sucrase cleaves sucrose into glucose and fructose, the inhibition of which control the conversion of disaccharides into simple sugars. In the present study GTFE inhibited α-amylase activity.

Effect on 3T3-L1 Cell Viability

Figure 3:
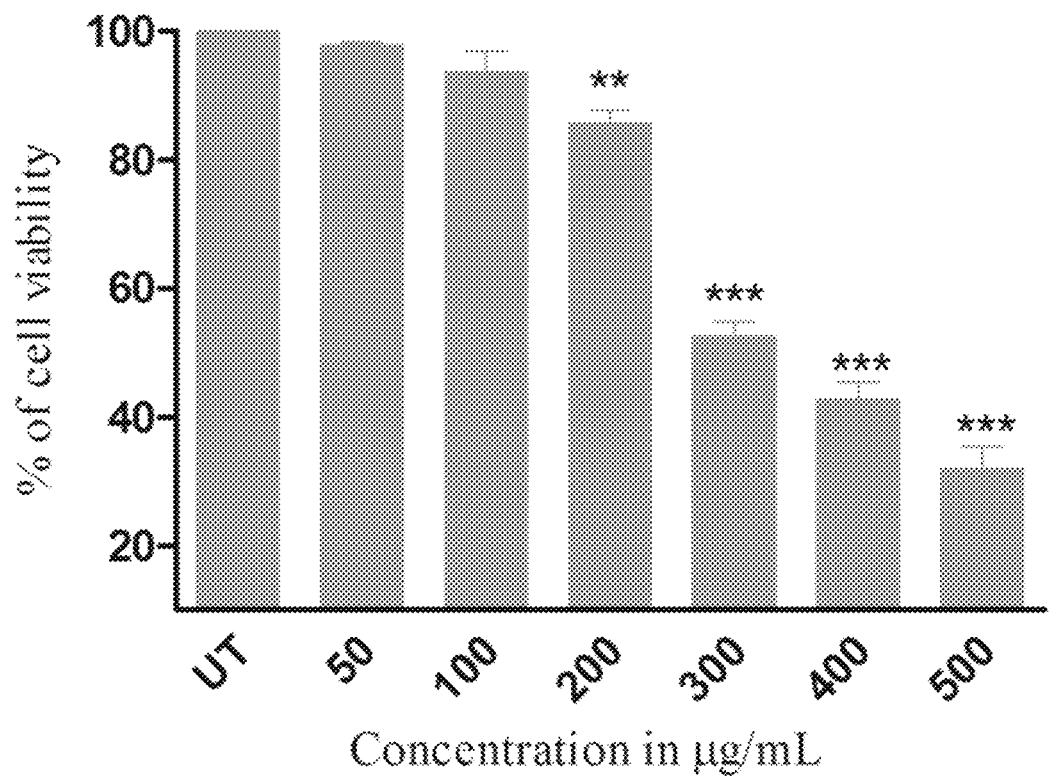
FIG. 3 is a graph showing the effect of an embodiment of the inventive composition on the viability of 3T3-L1 pre-adipocytes.

MTT assay results showed reduction in viability of 3T-3L1 cells after GTFE exposure in a dose dependent manner, showing less viability at higher extract concentrations. The IC50 value was determined to be ~292 µg/ml after 48 h of exposure (FIG. 3). For further study on dose-dependence, 150 µg/ml and 250 µg/ml doses of GTFE were taken.

Effects on Adipogenic Differentiation

Figure 4A:
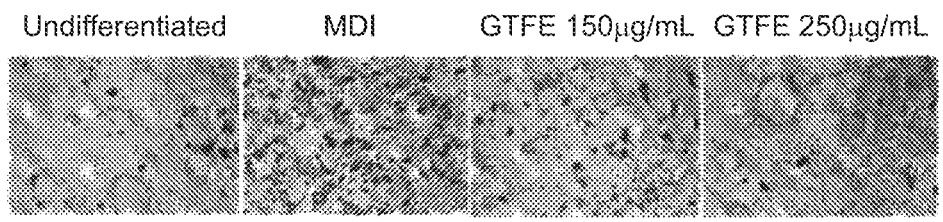
FIG. 4A depicts micrographs showing the anti-adipogenic effect of an embodiment of the inventive composition as determined by Oil Red 0 staining.
Figure 4B:
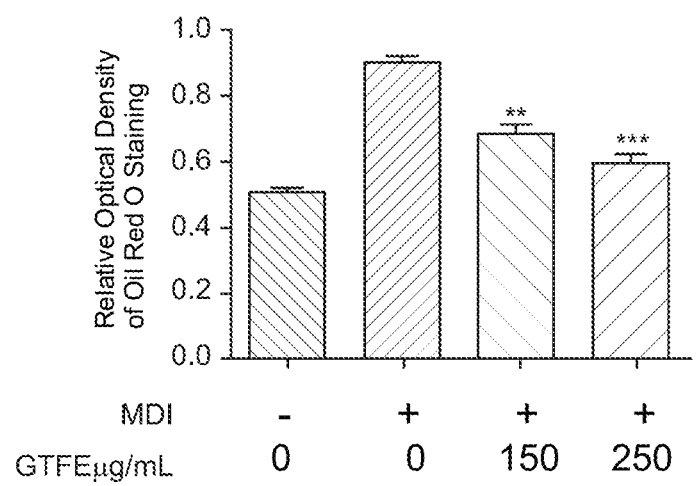
FIG. 4B is a graph showing the anti-adipogenic effect of an embodiment of the inventive composition as determined by lipid content.

In order to investigate the effects of GTFE on preadipocyte differentiation, lipid accumulation was measured by Oil Red 0 staining assay. As shown in FIGS. 4A and 4B, 250 µg/mL of GTFE suppressed lipid accumulation in 3T3-L1 adipocytes at levels that were statistically significant (p<0.05), showing that GTFE can inhibit adipogenesis in 3T3-L1 cells. The use of differentiation of undifferentiated fibroblasts (pre-adipocytes) to mature adipocytes, which is termed adipogenesis, is a central area of obesity research. The main characteristics of cellular adipogenesis are continuous fat mobilization and subsequent cell morphological changes in size and shape. During adipogenesis, fat droplets accumulate in adipocytes and cells become more insulin-responsive. Also, gene expression of fat-related factors are changed. In this study, the ability of the composition of the invention to inhibit the mechanism of adipogenesis was observed.

Effects on PPARγ and C/EBPα

Figure 5:
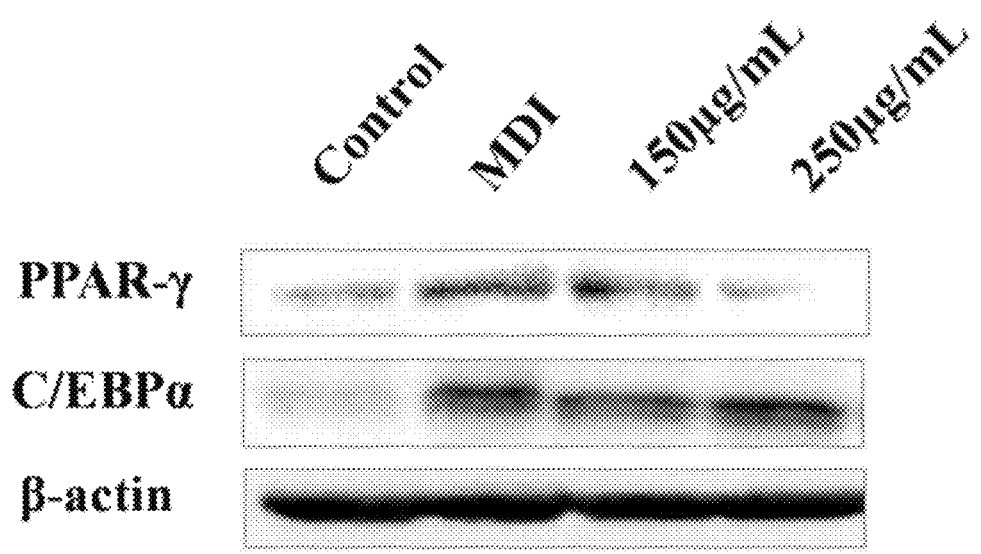
FIG. 5 is a Western blot showing the effect of an embodiment of the inventive composition on the expression of PPARγ and C/EBPα on day 8.

In order to investigate anti-adipogenesis, it was demonstrated that GTFE treatment resulted in a dose-dependent suppression of the protein levels of PPARγ and C/EBPα (FIG. 5). These results indicated that GTFE treatment inhibited the expression of PPARγ and C/EBPα at the protein level demonstrating that GTFE inhibited adipogenesis by suppressing the transcriptional factor cascade. It has been reported that adipogenesis is a complex process which is tightly regulated by sequential activations of various transcriptional factors. Preadipocyte culture systems are well established for studying cellular and molecular mechanisms of adipocyte differentiation. Adipokines, such as C/EBP α and PPARγ, are some of the most important genes during adipogenesis and have a direct impact on the development of fat cells.

CONCLUSION

The present findings show that the inventive composition can scavenge free radicals, inhibit the enzymes responsible for lipid metabolism, and inhibit adipogenic differentiation of 3T3L-1 cells. These findings demonstrate that the composition can modulate molecular events in 3T3-L1 preadipocytes and thus provide a treatment for obesity.

The invention claimed is:

1. A method of suppressing the expression of PPARγ and C/EBPα in a subject, comprising administering to the subject an effective amount of a composition comprising an aqueous alcohol extract of flowers from *Camellia sinensis*, wherein administering said composition promotes a healthy body weight in said subject.

2. The method of claim 1, wherein said extract has at least one of (i) an IC50 value of about 120 μg/mL for pancreatic lipase in vitro, and (ii) an IC50 value of about 199 μg/mL for alpha amylase in vitro.

3. The method of claim 1, wherein said extract has an IC50 value of about 43 μg/mL for lipid peroxidation in vitro.

4. The method of claim 1, wherein said extract has an IC50 value of about 41 μg/mL as determined by DPPH radical scavenging assay.

5. The method of claim 1, wherein administering said composition reduces body weight in said subject.

6. The method of claim 1, wherein administering said composition prevents or inhibits weight gain in said subject.

7. The method of claim 1, wherein administering said composition maintains said subject's body weight.

8. The method of claim 1, wherein administering said composition reduces body fat in said subject.

9. The method of claim 1, wherein administering said composition prevents or inhibits body fat gain in said subject.

10. The method of claim 1, wherein said subject is overweight.

11. The method of claim 1, wherein said subject is obese.

12. The method of claim 1, wherein said composition is administered at a dose of about 50 mg per kilogram of bodyweight, about 100 mg per kilogram of bodyweight, about 150 mg per kilogram of bodyweight, or combinations thereof.

13. The method of claim 1, wherein said composition is administered one or more times.

14. The method of claim 1, wherein said composition is administered daily, weekly, monthly, or combinations thereof.

15. The method of claim 1, wherein said composition is administered in a form selected from the group consisting of a powder, liquid, pill, tablet, pellet, granule, capsule, soluble film, solution, spray, syrup, linctus, lozenge, pastille, chewing gum, chew, paste, vapor, suspension, emulsion, ointment, cream, lotion, foam, liniment, gel, drop, topical patch, buccal patch, bead, gummy, gel, sol, injection, and combinations thereof.

16. The method of claim 1, wherein said composition further comprises at least one of a vitamin, mineral, amino acid, protein, carbohydrate, lipid, fatty acid, excipient, pharmaceutical carrier, bulking agent, binding agent, caffeine, flavoring, sweetener, and preservative.

17. The method of claim 1, wherein said composition is selected from the group consisting of a food, snack, nutritional supplement, dietary supplement, food supplement, beverage, and combinations thereof.

18. The method of claim 1, wherein said composition is administered systemically.

19. The method of claim 1, wherein said composition is administered by a route selected from the group consisting of orally, buccally, sub-lingually, and combinations thereof.

20. The method of claim 1, wherein said composition is administered orally.

21. The method of claim 1, wherein said subject is a human.

* * * * *